United States Patent [19]

Bartos et al.

[11] Patent Number: 4,619,903

[45] Date of Patent: Oct. 28, 1986

[54] PROCESS FOR CARRYING OUT SEROLOGICAL INVESTIGATIONS ACCORDING TO THE PRINCIPLE OF THE COMPLEMENT FIXATION TEST, AND TEST PACKAGES FOR USE IN THIS PROCESS

[75] Inventors: Dezzö S. Bartos, Solingen, Fed. Rep. of Germany; Denis Fitzpatrick, County Cork, Ireland

[73] Assignee: Harcourt House, Dublin, Ireland

[21] Appl. No.: 485,064

[22] Filed: Apr. 14, 1983

[30] Foreign Application Priority Data

Apr. 21, 1982 [IE] Ireland ................................... 943/82

[51] Int. Cl.$^4$ ................ G01N 33/566; G01N 33/563; G01N 33/557; G01N 53/00
[52] U.S. Cl. .................................... 436/517; 436/501; 436/512; 435/4; 435/7; 435/12
[58] Field of Search ............... 436/501, 512, 517, 821; 435/7, 4, 12

[56] References Cited

U.S. PATENT DOCUMENTS 3,977,944  8/1976  Müller-Matthesius ................. 435/4
4,218,535  8/1980  Ray ....................................... 435/12
4,476,230 10/1984  Sieber .................................. 436/517

FOREIGN PATENT DOCUMENTS 2333434  1/1975  Fed. Rep. of Germany .
1487351  9/1977  United Kingdom .

OTHER PUBLICATIONS

Vargues et al., Kinetics of Complement Fixation in the Determination of Australia Antigen, presented at the Technicon International Congress, Nov. 2–4, 1970, New York–supported by a grant to the Eduaros Research Foundation, Inc., Copyright 1971, by Thurmann Associates, Miami, Fla.

*Primary Examiner*—Christine M. Nucker
*Assistant Examiner*—Stephen C. Wieder
*Attorney, Agent, or Firm*—Wegner & Bretschneider

[57] ABSTRACT

Serological investigations according to the principle of the Complement Fixation Test (CFT) can be evaluated by means of a kinetic method by using an excess of complement. Preferably the amount of the complement in the reagents and the control samples are balanced against one another.

9 Claims, 4 Drawing Figures

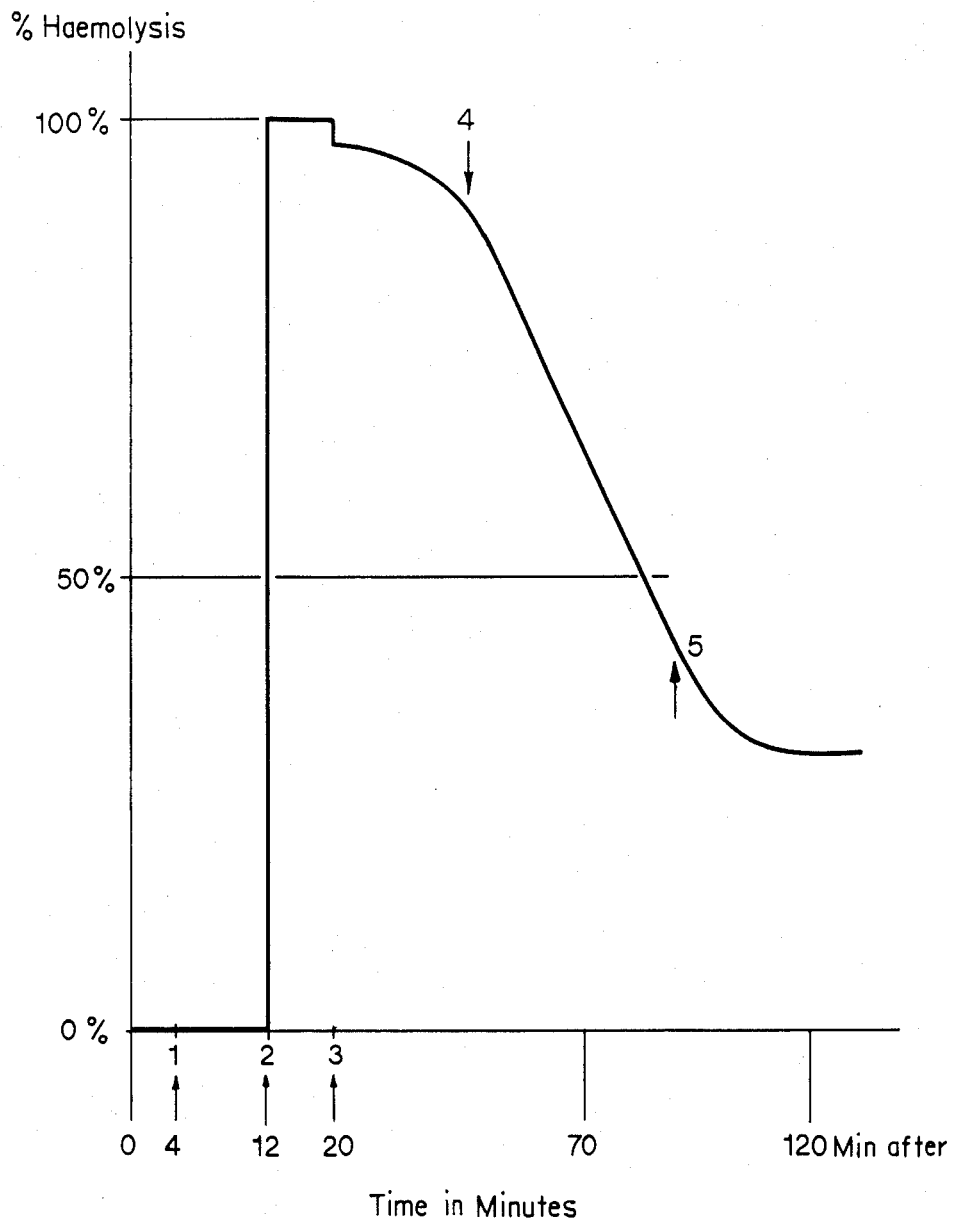

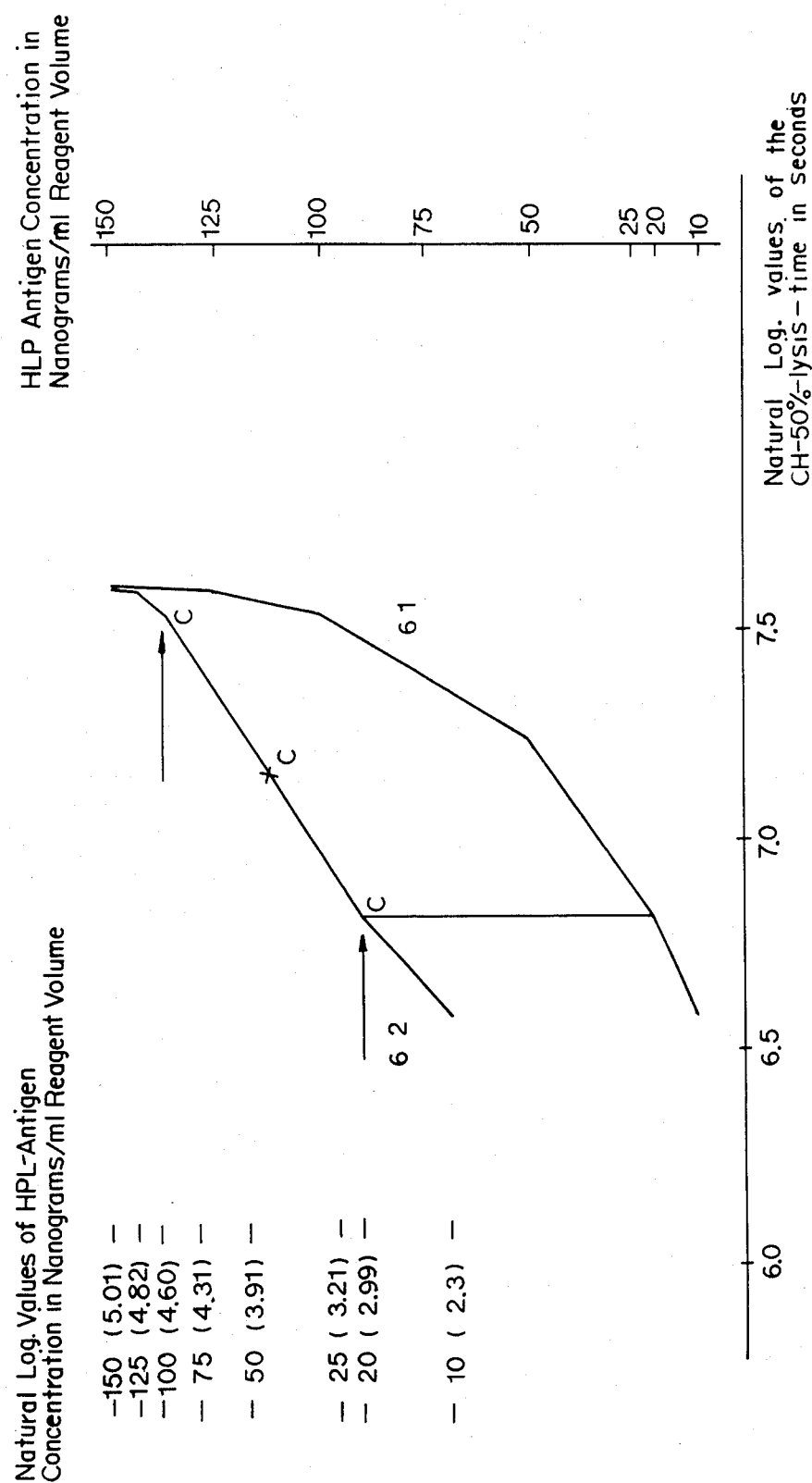

PROCESS FOR CARRYING OUT SEROLOGICAL INVESTIGATIONS ACCORDING TO THE PRINCIPLE OF THE COMPLEMENT FIXATION TEST, AND TEST PACKAGES FOR USE IN THIS PROCESS

The invention relates to a process for carrying out serological investigations according to the principle of the Complement Fixation Test and ready for use test packages for use in this process. British Patent Specification No. 1487351 relates to the principle of a mono-test system.

During the development of the technical production of this method observations were made and developed, and these form the basis of this patent application. These observations are set out below.

The classical Complement Fixation Test was discovered at the beginning of this century. Surprisingly in the intervening years the technique has not been greatly improved. The reaction consists of two parts: In the first part of the test an antibody (e.g. natural antibody in a patient's serum) reacts with an antigen (e.g. with a virus antigen) in the presence of a fixed amount of complement. The immunocomplex which results from the reaction of the antibody with the antigen binds complement activity. In the second part of the test, the lysis or non lysis of antibody (Amboceptor) sensitised sheep-erythrocytes, made visible by the so called complement haemolytic reaction, is measured. In the case of an antibody antigen reaction (the patient has been exposed to viral infection) the resulting immunocomplexes bind the complement activity and the sheep-erythrocytes remain unlysed due to the absence of complement activity. If the reaction is negative the added complement activity remains, a complement mediated haemolysis of the sheep-erythrocytes occurs, and the turbidity of the reactant mix decreases. Quantification of the reaction could only, up to the present be achieved, by serial dilution, usually of the serum sample, whereby each dilution is checked for a positive or negative reaction. A number of photometric methods for the complement fixation test have been described, but all of these methods, including those which appeared in recent years in handbooks, are characterised by a basic deficiency; only a grading of the complement haemolysis is measured photometrically (partial haemolysis methods). In this method only the amount of blood colorant released is measured. Even if with these methods a sensitivity range of just a few nanograms of antigen substance/ml reactant can be operated these methods contain many disadvantages. These are:

(1) It is very difficult to stop the reaction. One presently known way is e.g. by centrifuging and thereafter measuring the amount of released red blood colorant and (2) the measurement range remains permanently limited to the range of lysed or unlysed condition of a reaction mixture which has been previously determined for all time.

The term "analytical test system" as used herein includes the use of antigen or antibody as the analytic test medium.

The term "control test system" as used herein includes the use of antigen or antibody as the analytic test medium.

The invention is directed towards providing a process for carrying out serological investigations that will overcome these difficulties.

Figure 1:
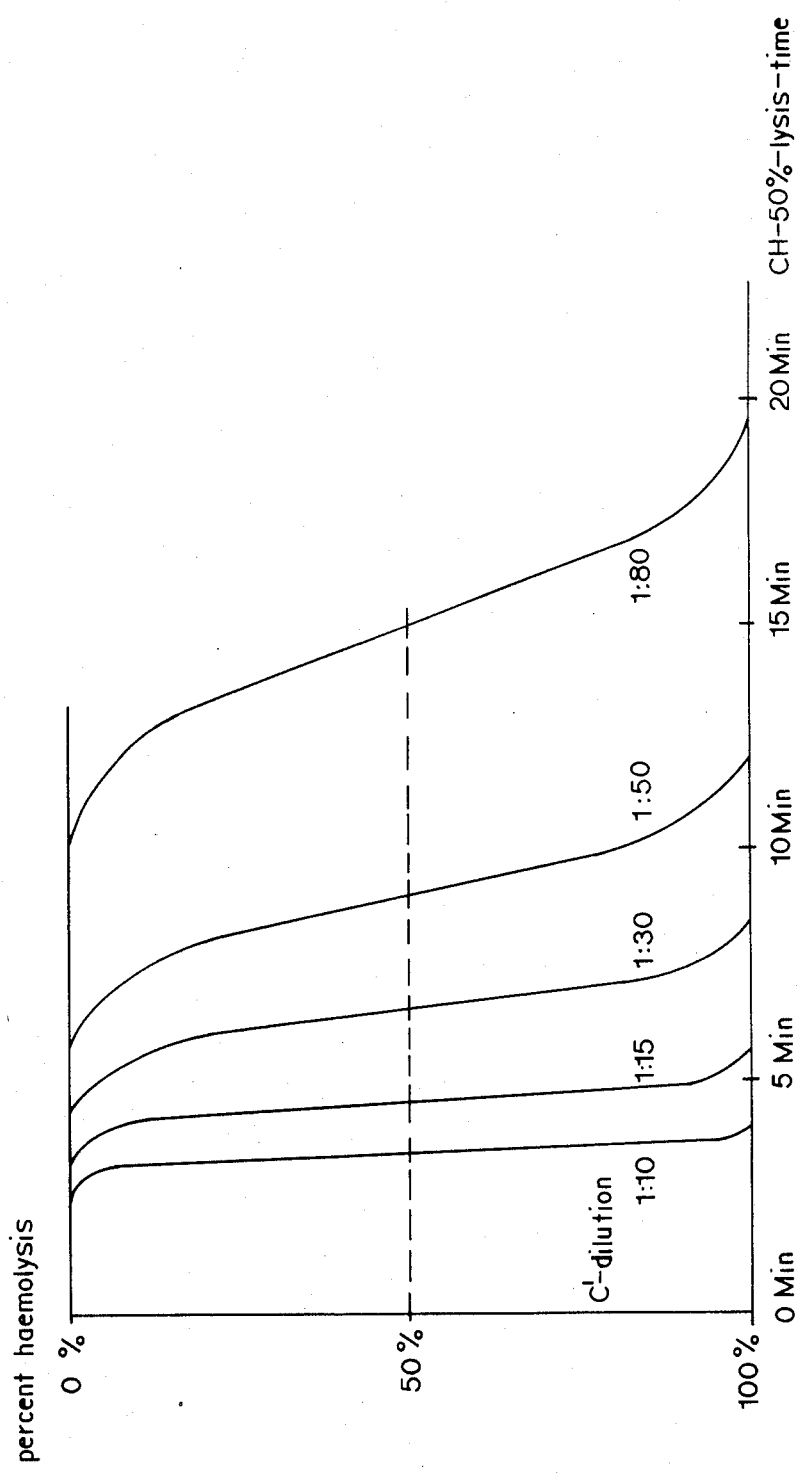
FIG. 1 is a graphic representation of optimized photometric measurements for the estimation of complement activity at different solution concentrations of complement.

FIG. 3 shows a curve depicting the kinetics of complement consumption according to Vargues et al. The points identified along this sigmoidal curve are as follows: pt. 1—antigen is added to the buffer, pt. 2—an excess of complement is added to the system, pt. 3—antibodies in excess are added to the system, the slope of the reaction between pts. 4 and 5 gives the rate constant of complement consumption.

FIG. 4 presents a linear standard curve for antigen/antibody reactions. It shows the natural log of the CH-50% lysis time in seconds on the x-axis against both a direct display of the antigen concentration and a logarithmic display of antigen concentration on the y-axes. The linear progression of the antigen standard curve is shown between the arrows in the range 20-100 nanogram HPL/ml. Line 6(1) shows a semilogarithmic display and 62 shows double logarithmic display.

According to the invention there is provided a process for carrying out a serological investigation according to the principle of the Complement Fixation Test wherein a complement excess is used and the evaluation of the reaction is carried out by a kinetic method. A further object of this invention is that the amount of complement in the reagents and the control samples are balanced against one another. The invention also provides a ready to use test package for carrying out the serological investigation wherein to carry out the reaction reagents are used, that are stored in a stable form and whose activities are balanced against one another, whereby the reagents are manufactured in one package individually, partially together, or preferably all together in one ampoule pair for the analytical system and for the control system.

In one embodiment, the invention provides a process for the optimized visual execution of the complement fixation test, wherein reagents are preserved in a solid form in such a way that by the use of suitable procedures one can produce, in the negative control or in the blank after completion of main incubation, identical complement activities, before initiation of the haemolysis reaction (indicator reaction), both in the analytical system and in the control system. The results of the reaction are evaluated. A delay in haemolysis is considered to be a positive reaction and measurement of the degree of delay in haemolysis can be used to quantify the reaction.

Preferably in the process the synchronization of actual complement activity in the analytical and the control system is achieved in that (a) high quality reagents are used that exert no influence on the actual complement activity or (b) the unspecific effect in analytical and test systems caused by other reagents apart from the complement source is as small as possible and identical in both systems, or (c) by addition of a higher concentration of complement into the system with the higher anticomplement activity in order to compensate and balance out the lower actual activity in comparison to the other system, or (d) the system with the higer complement activity is sufficiently diluted at the beginning of the main incubation but before beginning the binding of antibody an antigen preferably immediately after the solution of the preserved solid (deep frozen or freeze dried) reagents with a suitable buffer, so that at the end of the main incubation in both the analytical and control system in the case of a negative reaction (blank or use of negative control serum as test), but before beginning the indicator reaction identical actual complement activities exist.

The invention further provides a process for quantifying the Complement Fixation Test wherein the reaction is carried out using reagents preserved in a solid form, in such a way, that after completion of the specific antibody/antigen reaction determined complement activity in the analytical and in the test system, an excess of complement exists, and the remaining complement activity of the various systems is backtitrated by suitable method, preferably the CH-50%-lysis-time-analysis with allowance for the latent phase of the complement haemolysis and the resulting lysis times, and the antigen or antibody concentration are transformed into their natural logarithmic values and plotted against one another giving preferably a linear standard curve.

In addition, the invention provides a description of normal commercial antigen/control antigen or antisera and blank sera intended for carrying out a serological investigation according to the principle of the Complement Fixation Test in such a way that by allowing for this additional description or details of the anti-complement activity of these reagents in a test the principle and the usability of this invention is possible without the user having to undertake further preadjustments.

These disadvantages are overcome by the new method. If the complement haemolysis is monitored photometrically (FIG. 1) preferably by measuring turbidity at the wavelength of 546 nm (or near this wavelength) under experimental conditions including 0.1 ml complement dilution 1:x, 0.1 ml Ambozeptor 1:500, 0.8 ml NaCl-buffer, incubated for 10 min. at 37° C. incubated, with the addition of 0.1 ml indicator erythrocyte with a 50—50%-lysis-time analysis, a number of basic rules of the complement haemolysis can immediately be recognized, that can be exploited for the optimization of the Complement Fixation Test:

The complement haemolysis follows a sigmoidal reaction curve. After a latent time, which is longer or shorter depending on the amount of complement activity present, a lysis reaction occurs (release of red blood colorant from the sensitised erythrocytes with a resultant decrease in turbidity, increasing transmission of the reaction mixture, decreasing the extinction or absorbance).

The higher the complement activity in the reaction mixture the greater is the slope of this sigmoid reaction curve, the lower the complement activity the flatter is the lysis curve.

If the complement activity is used then the red blood-cells remain unlysed and the turbidity of the reaction mixture remains unchanged (corresponding to a positive reaction in the classical Complement Fixation Test). The turbidity (extinction/absorbance) of the reaction mixture new decreases gradually and slowly, corresponding to the gradual sedimentation of the unlysed erythrocyte suspension. From this the following facts can be ascertained:

(1) If one observes an original curve (FIG. 1) of complement haemolysis with increasing complement activity it would appear at first, as if a photometric Complement Fixation Test would be much more sensitive, if by a suitable quantification of the reaction, not only the status of lysed or unlysed condition of the reaction mixture at the right hand end of the curve of this test series were used to judge the course of the reaction of the Complement Fixation Test, as is normally the case in the classical CFT, but also if the intermediate steps of lysed and unlysed condition of the complement haemolysis were measured and suitably quantified.

(2) In addition it is apparent that in the well-known photometric evaluation method also the measurement of the release of red colorant, cannot be optimal (partial haemolysis measurement method), because this procedure is inconvenient and disadvantageous, and the stopping of the reaction and the separation of the unlysed erythrocytes is inconvenient. In addition, with this method only a narrow measurement range of the theoretical and practical available measurement range can be used. In addition one operates only in the range of partial haemolysis.

(3) The procedure of British Patent Specification No. 1487351 has enabled a considerable rationalization of the Complement Fixation Test, since it provides a ready to use monotest system which does not require pretesting although retaining all control possibilities through the use of ready to use stable reagents. Nevertheless it was not found possible to use the theoretical possibilities optimally as unspecific reactions could not be completely excluded.

(4) Further possibilities of optimizing the Complement Fixation Test can be adduced from the reaction kinetics. These are:

(a) A considerable extension of the measurement range, when a reaction technique is used which operates permanently in the range of complement excess i.e. kinetic evaluation technique.

(b) The manifold increase in the sensitivity of the reaction when this kinetic method is evaluated photometrically and this is combined with a suitable mathematical formula, so that in the desired measurement range the standard curve can be expressed as a regression line.

(c) Considerable elimination of unspecific effects on the specific reaction usually caused by the proband material as the nature of these unspecific influences can be analysed from the reaction curve and corresponding action taken.

It is evident that the measurement range of the Complement Fixation Test can be considerably extended if the complete extent of the complement haemolysis of a reactant mixture over time is utilized. A prerequisite is that the qualitative-quantitative evaluation of the Complement Fixation Test is not only determined by the ratio of lysed to unlysed cells but also must be extended to the delay in complement haemolysis. The decision as to whether this delay of complement haemolysis is visually-qualitative or semi-quantitatively measured or is analysed photometrically, and the results of this analysis used to quantify the results is left to the user. The main characteristic of the method is the kinetic measurement in the presence of excess complement. If the registration of the delay of complement haemolysis is measured visually, then measures must be taken, so that, in the case of a negative reaction (e.g. in the case that no antibodies in the proband serum exist against the added (virus)antigen) or that in the material to be studied none of the substance to be measured is present, the haemolysis reaction (decrease in extinction, decrease in turbidity) after completion of the main reaction bond (reaction of the antigen with the antibody and binding of complement activity in the analytical sample as also in the control sample) corresponding to antigen test and control antigen test, runs absolutely synchronized. When ready to use reagents according to the German Pat. No. 23 33 434 or an extended form of this corresponding to the extended range of the patent claims of the original patent application, the ready to use reagents are manufactured in an ampoule pair, or in a ready to use package, even when these ready to use ampoule pairs or packages contain only the necessary individually packed reagents for e.g. only complement and antigen or complement and control antigen or complement and an antibody against the substance to be tested e.g. complement and a blank serum (of the same species but not immunized individual or animal), and in the haemolysis reaction to the classical heamolytic system is used.

It is evident that a delay in the haemolysis reaction alone (desynchronization of the reaction) must be regarded as a positive result and as a consequence of this the Complement Fixation Test is increased in its sensitivity considerably.

This demand to guarantee that the haemolysis reaction is synchronized after the main incubation in the control and analytical system when the test is negative is essential also for the extended form of the reaction corresponding to the German Pat. No. 23 33 434. Preferably one will always use the additional disclosure of this specification and include also the amboceptor in the ready to use ampoule pair or in the reagent package to avoid laborious work required for the production of the classical haemolytic system.

From the detailed examples included it can be seen that this ideal situation and essential requirement for the achievement of the optimized visual Complement Fixation Test cannot be achieved by a simple mixing together of normal commercial reagents (antigens, control antigens, or antibodies and control serum) with complement and possible addition of amboceptor, because in most cases the reagents have differing unspecific anticomplement activities. These differing anticomplement activities, however, can be determined by the manufacturer of ready to use reagents in advance, they can be calculated and it is possible then at the production step or when the instructions are being devised to allow for these unspecific activities. Consequently the necessary synchronization of the haemolytic reaction in negative cases can be guaranteed to the user. There are three ways to guarantee that in negative cases the necessary resynchronization of the haemolytic reaction required for the optimization of the reaction occurs.

1. One uses high quality reagents as e.g. a highly purified Rubella Complement Fixation Test antigen and control antigen from tissue culture, whereby antigen/-control/antigen are further purified with an ultracentrifuge, whereby the highly purified reagents exert absolutely no unspecific effect on the actual complement activity of the reaction mixture.

2. Or one balances out this unspecific effect on the actual complement activity which in most cases corresponds to an unspecific consumption of complement activity in such a manner that by increasing the amount of complement activity this unspecific consumption can be balanced out at the production stage of the ready to use reagents. Alternatively one corrects the unspecific complement consumption by carrying out the reaction in such a way, that one further dilutes, according to a definite factor, with a suitable buffer solution the reagent mixture with the higher complement activity after the main binding in the negative control test. This would be carried out preferably before beginning the main binding reaction, i.e. immediately after dissolving the ready to use reagents before the test is begun and as a result of that obtain the desired synchronization in the negative control test. This dilution factor is determined by the manufacturer and is indicated in the instructions relating to the individual charge. The final step of the synchronization of the haemolysis curve of the negative control test is then carried out by the user himself.

In the case of the optimized visual Complement Fixation Test it is preferable to carry out the reaction on a microtiterplate which if possible is warmed to 37° C., the optimal temperature for the Complement Fixation Test and one uses in this case preferably an optical aid. This optical aid is a finely patterned transparent underlay which makes it possible to determine the delayed haemolysis the desynchronization of the reaction more exactly and with a higher resolution not just qualitatively but also semiquantitatively. In practice it has been found that delays of 20 to 40 seconds can reproducibly be determined. This delay in haemolysis corresponds to 10 to 15 nanogram complexed antigen per ml reaction mixture and corresponds to an approximately 10-fold increase in the sensitivity of the reaction compared to the classical Complement Fixation Test.

The manufacturer of the ready to use reagents will preferably so adjust the reagents that a complete phase shift of the haemolysis reaction corresponds to a 1:5 positive dilution of the classical Complement Fixation Test in order that comparisons of titer can more easily be made. For the photometric quantification of the Complement Fixation Test from ready to use reagents the most suitable method of measurement is the so called 50% complement haemolysis measurement: the method of CH-50%-lysis-time-analysis. An alternative method is the measurement of the slope, extinction or turbidity decrease per unit time to obtain a haemolysis curve and on the basis of this to establish a quantification of the reaction. This latter method, however, has the disadvantage of the classical Complement Fixation Test: the measurement range of the reagents is once again limited to a haemolysis phase (unlysed/completely lysed) and one loses the possibility of a wide measurement range including the latent phase of the haemolysis reaction.

Figure 2:
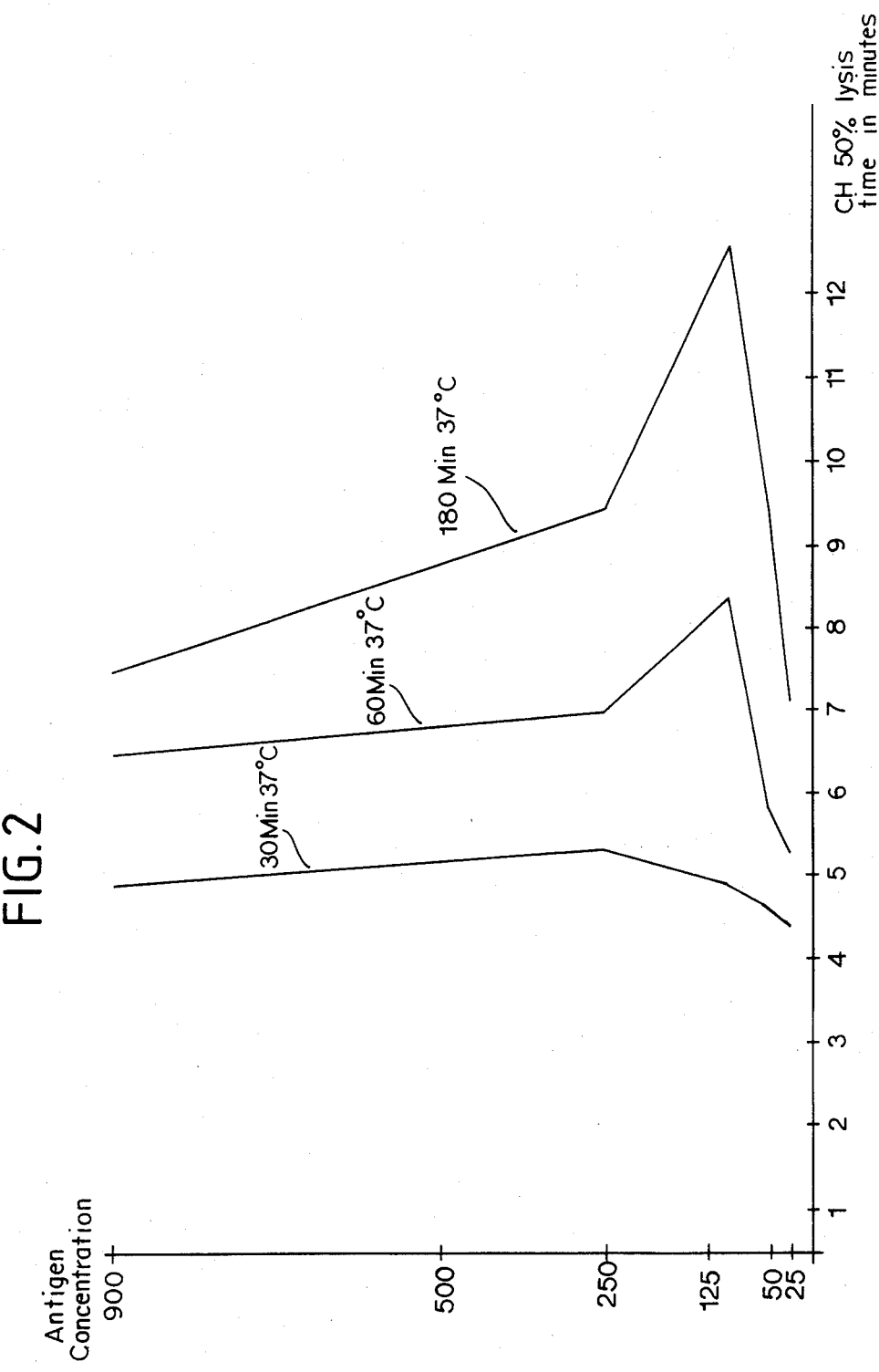
FIG. 2 is a representation of an antigen/antibody standard curve, plotting complement activity vs. concentration of antigen tested. The antigen concentration is based upon a program transferrin-antigen/2 ml reagent volume.

The CH-50%-lysis-time-analysis method is in fact a method to measure the actual complement activity of a reaction mixture and on its own does not provide an excellent photometric quantification of the Complement Fixation Test. For this one needs a transformation of the measured lysis time, preferably in seconds, to their natural logarithmic values and the display of the concentration of the tested antigen or antibody amount, likewise in its natural logarithmic value. This procedure is called the double logarithmic method of evaluating the measurement results. This preferred procedure achieves considerable advantages. FIG. 2 indicates such an antigen/antibody standard curve. The experimental conditions of FIG. 2 include 0.1 ml of complement 1:10, 0.1 ml of Ambozeptor 1:500, 0.1 ml anti-human tranferrin from rabbits 1:100, 0.1 ml transferrin-antigen, 0.6 ml NaCl-buffer, at an incubation of 37° C. for $t_x$ with an addition of 0.1 ml of indicator erythrocyte suspension E 0,5.

From this certain parameters of the complement fixation by specific antibodies/antigen reagents can be determined which one can use to optimize the reaction:

1. In antibody excess with addition of increasing amounts of corresponding antigen a definite amount of complement active immuno complexes are required (in statu nascendi), before a measurable complement fixation reaction takes place. Experience has shown that this happens at an antigen concentration of 15 to 25 nanogram/ml reagent mixture.

2. When this point is reached a specific binding of complement takes place according to a strict parameter which is described by the following formula $$k_{37} = 2.3 \frac{1}{t} \frac{1}{D} \log \frac{C_o}{C_t} Q_{10} \frac{(37 - T)}{10}$$

where t is the incubation time of the complement fixation in minutes, D the dilution of antibody or antigen, $C_o$ the initial complement concentration, $C_t$ the complement concentration at time t, $Q_{10}$ is the temperature coefficient, and T is the incubation temperature.

This equation according to R. Vargues, G. Vargues and S. Vernance: Kinetics of complement fixation in the Determination of Australia Antigen Presented at the Technicon International Congress, Nov. 2-4, 1970, New York-Supported by a grant to the Eduaros Research Foundation, Inc. Copyright 1971 by R. Thurmann Associates, Miami, Fla.: 1-5, can be transformed into the rate constant k=rate constant of complement fixations reaction. If a system (FIG. 3) consisting of complement and antibody has antigen added consumption of complement begins immediately. If this is indicated graphically the kinetics of the reaction yield a sigmoidal curve (FIG. 3). The slope of this curve is characteristic for each antibody/antigen relation at a constant initial complement activity.

The relation between the concentrations of the reagents with one another can be expressed by the mathematical equations $$C_f = C_o(1 - e^{-kDt}) \quad \text{equation 1}$$

and $$C_t = C_o e^{-kDt} \quad \text{equation 2}$$

where $C_f$ is the concentration of free complement, $C_t$ the concentration of bound complement, k is the rate constant of complement binding, D is the dilution of antiserum, and t the time of complement binding from the beginning of the reaction. This formula and observation were determined by Vargues et al., however, with the technique of partial haemolysis: A change in the antibody/antigen ratio causes an alteration of the rate constant of the complement binding. With increasing antigen concentration and holding other variables constant a linear increase in the rate constant of the complement binding up to an optimal antibody/antigen ratio can be observed. This point corresponds to the optimal binding capacity of the given antibody amount in the reaction mixture when allowance is made for complement consumption during simultanuous binding of the antigen. Further increases in the antigen concentration cause the rate constant of complement binding to decrease somewhat symmetrically with the previous increase in the rate constant in antibody excess. At high antigen excess hardly any complement is bound at all.

These parameters were determined by Vargues et al. in the partial haemolysis range and corresponds in their quantitative composition to the results of the chessboard titration of the classical Complement Fixation Test. The firm Technicon had developed at the beginning of the 70's and brought on the market automatic equipment for the Complement Fixation Test based on this technique. This method was also afflicted by the disadvantages of partial haemolysis. The Technicon autoanalyzer attempted to circumvent this by using changes in the length of tubing to vary the reaction time in order that the reaction mixture was always in the range of partial haemolysis when it reached the detection system.

3. It is a novel and new discovery that after completion of the specific antibody/antigen reaction which causes complement binding and which experience has shown to be completed after 180 minutes at 37° C. main incubation corresponding to the kinetics of the reaction that in the reagent mixture for a certain time thereafter (30-60 minutes), the remaining actual complement activity corresponds to the amount present after the completion of the specific reaction. This phenomenon has been proved in serial tests in which the ratio of the reagents with the exception of the concentration of one substance (e.g. antigen) or an antibody are identical. This condition makes possible the photometric quantification or the semiquantitative visual quantification of the Complement Fixation Test in its kinetic evaluatable form (always working with excess complement) in a manner that with the assistance of the CH-50%-lysis-time-analysis in the individual tests, e.g. in the antigen substance standard curve test and in a sample test (determining antigen concentration of the sample), the actual complement activity shortly after completion of the antibody/antigen determined specific complement binding can be quantitatively determined and from the individual actual complement activity values a quantification can be carried out.

The actual complement activities in the individual tests are long term effects/summation products of the antigen/antibody reaction and the bound complement corresponding to the quantification according to Vargues et al. with the advantage that the evaluation/quantification of complement binding is independant of the haemolysis reaction (it is not carried out in the range of partial haemolysis), but rather the quantification of the reaction is carried out in a wide measurement range of a reaction mixture, including the latent phase of complement haemolysis, directly upon, or preferably after conclusion of the antibody/antigen determined complement binding.

If an evaluation in this way is carried out later than 180 minutes (+ca. 30-40 minutes) after the beginning of the reaction then with delayed evaluation, a disturbance of the strict quantitative reaction results would occur in the individual tests due to the unspecific further inactivation of the complement system in the reactant mixture of the individual tests. Premature reading of the results of the reaction means that specific complement binding is not completed. The parameters would be only partially valid, the standard curve would not have a linear form, and the reaction would be less sensitive. Naturally measurement of the actual complement activity is not tied absolutely to the point of 50% decrease of the haemolysis reaction, although this point can be regarded as optimal and should preferably be used. It is possible to carry out a quantification in the range 20%-80% lysis of the indicator erythrocyte system so long as the reading in each test is carried out at the same stage of the haemolysis reaction.

When quantifying the antibody/antigen determined complement binding the ratio of reagents is preferably so chosen that the equivalent point (the point of optimal antibody/antigen ratio for the complement binding) is in the range 15-20 minutes.

Furthermore the reaction system is preferably pre-sensitized with small amounts of antigen or antibody, so that the blank indicates and exceeds the point of the C+1 inactivation system. In this way one can immediately measure the smallest amounts of the substance being tested that is possible on the basis of the reproducability of the reaction (ca. 1.5-5 nanogram antigen/ml reactant mixture). This is called the method of limited immunocomplex-/substance technique. By this method one achieves a linear standard curve for antigen/antibody, if one uses this method of evaluation: the natural logarithmic values of the CH-50%-lysis-time-analysis corresponding to the actual complement activity are plotted against the antigen/antibody concentration, whereby these are also displayed in their natural logarithmic values. In this case all one needs in this measurement range is a blank value, a control value, and an analytical value. The control contains sufficient test substance, so that this simultanuously indicates the equivalent point of the measurement system (highest possible measurement point/substance concentration for the test). In this case one can determine the unknown concentration by the use of a simplified formula $$c = \frac{c_1}{t_1} \times t^F$$

$$\text{Factor } (F) = \frac{\ln c_2 - \ln c_1}{\ln t_2 - \ln t_1}$$

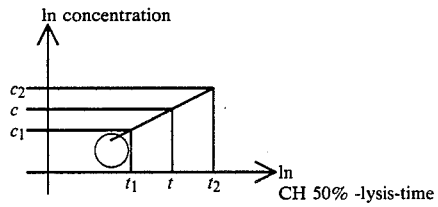

where C is the unknown concentration, $c_1$ preferably the blank value ($B_o$) with a fixed amount of the antigen being measured so that the complement system is pre-sensitized over the level of the C-1-inactivator-system, t is the CH-50%-lysis-time of the sample in seconds and F is a factor. In the calculation of the factor (F) the known concentrations in nanogram/ml and the corresponding CH-50%-lysis-time in seconds are transformed into their natural logarithms.

Serial analysis of human serum samples have indicated that the majority of proband sera contain a so called amboceptor-like activity in small to large amounts. This amboceptor-like activity of the proband sera influences unspecifically the actual complement activity of the individual test in such a way that the test with the proband serum exhibits a higher actual complement activity in comparison to the blank, because this value is a function of the complement concentration and the degree of sensibilization of the indicator erythrocytes.

It is evident, that this unspecific effect of proband serum can be eliminated if one absorbs the proband serum with a fixed amount of sheep-erythrocytes after the normal inactivation at 56° C. for 15-30 minutes in order to remove these amboceptor-like antibodies from the sample. For this purpose stablilized sheep-erythrocytes are preferably used. In these cases one can include the inactivation step of the samples own complement activity with the absorption. For this purpose sheep-erythrocytes washed and stabilized with Formalin or glutaraldehyde are preferably used. Experience has shown that ca. 100-200 microliters erythrocyte sediment pro ml proband serum are sufficient, to completely eliminate the amboceptor-like activity of the serum samples. Serum samples treated in such a way only show an inhibitory effect, which delays the haemolytic reaction, this being caused by an unspecific inhibition of the actual complement activity to a greater or lesser degree. Naturally a proband serum that contains circulating immunocomplexes due to illness will cause a complement binding which is due to the complement binding capacity of the immunocomplex. This complement binding is, however, in the analytical (antigen) and in control (antigen) system in similar concentration. This causes a delay in the complement haemolysis because of the lower actual level of complement activity following the main binding but it does not cause a desynchronization of the haemolysis reaction which would be evaluated as positive. If one uses a standard serum, one can then by comparing the haemolysis delay in the control of the proband serum with a blank control recognize those serum samples which have a pathologically high anticomplement activity, when one uses the unspecific complement consumption of the standard serum as a reference system. Instead of sheep-erythrocytes also an extract therefrom can be used. Extracts can be made by centrifuging lyzed erythrocytes in 3 molar potassium chloride solution. After 16 hours it is dialyzed against 0.9% sodiumchloride solution. The residue is bound to carboxycellulose or sepharose which are inert against complement. In the optimized visual Complement Fixation Test one uses preferably inactivated and absorbed proband serum which does not possess amboceptor-like activity.

It is to be expected that in the classical complement fixation where the amboceptor-like activity of proband serum is not removed that this amobozeptor-like activity had a disturbing effect on the cause of the reaction, especially with the early dilutions where the proband serum content pro ml reagent is relatively high.

EXAMPLE 1

Demonstration of the various amboceptor-like activities of proband serum and the demonstration of the absorption/removal of these study factors by pre-treatment of the proband sera.

A test system for measuring the unspecific total effect of proband sera on the actual complement activity of a reactant mixture consisting of amboceptor and complement in optimal concentration (Serobac-complement-deviation-test I) 1 ml of reagent mixture containing 50 microliter complement in phosphate buffered saline with calcium and magnesium (PBS phosphate buffered physiological salt solution with a 10 mg% calcium and 5 mg% magnesium) and 0.2 microliter amboceptor 1:4000 (product of Behringwerke AG, D-3550 Marburg). To this reactant mixture 100 microliter of human proband serum, which had complement removed, at 56° C. for 30 minutes, was added and the mixture incubated at 37° C. for 180 minutes. A test with 100 microliter buffer solution instead of proband serum served as control. After incubation at 37° C. for 180 minutes corresponding to the main incubation of the Complement Fixation Test a CH-50%-lysis-time-analysis was carried out to determine the actual complement activity of the system. Sheep erythrocytes 100 microliter were added to give to initial extinction of 0.5.

|  | Results: CH—50%-lysis-time-analysis | | | | | |
|---|---|---|---|---|---|---|
|  | serum sample | | | | | |
| blank | 1 | 2 | 3 | 4 | 5 | 6 |
| 302 seconds | 420 | 255 | 485 | 300 | 415 | 370 |

Serum samples were found to possess a higher complement activity despite removal of complement than the control system possesses.

The same sera were analysed in a test system as above, however, without addition of amboceptor. For this the same source of complement was used.

|  | Results: CH—50%-lysis-time-analysis | | | | | |
|---|---|---|---|---|---|---|
|  | serum sample | | | | | |
| blank | 1 | 2 | 3 | 4 | 5 | 6 |
| unsolved | 880 | 445 | 1034 | 670 | 1800 | 990 |

The control system remains unsolved. This is to be expected as the system does not contain amboceptor. No sensitization of the sheep-erythrocytes can occur.

The proband sera show different amboceptor-like activities. So it is understandable that in the first series of studies the proband sera mimics a higher actual complement activity.

Absorption of proband sera with sheep-erythrocytes to remove this amboceptor-like activity:

To 800 microliter proband serum, inactivated for 30 minutes at 56° C., 200 microliter of a 50% washed human sheep-erythrocyte suspension resuspended in PBS-buffer was added, allowed to stand for 10 minutes at room-temperature and finally centrifuged. The supernatant forms the pretreated (decomplemented and absorbed) proband serum.

Both of the previous series of studies were repeated with pretreated proband serum.

Results of the test to measure the amboceptor-like activity—CH-50%-lysis-time

|  | acitivity - CH—50%-lysis-time | | | | | |
|---|---|---|---|---|---|---|
|  | proband sera | | | | | |
| control | 1 | 2 | 3 | 4 | 5 | 6 |
| unsolved | all probandsera were completely free of haemolysis after 30 minutes at 37° C. | | | | | |

Judgement: The above-described pretreatment of proband sera is sufficient normally to remove the disturbing amboceptor-like activity of proband sera completely.

Results of the test to determine the unspecific effects of pretreated proband sera on the actual complement activity of the test system.

|  | CH—50%-lysis-time | | | | | |
|---|---|---|---|---|---|---|
|  | proband sera | | | | | |
| Control system | 1 | 2 | 3 | 4 | 5 | 6 |
| 315 seconds | 370 | 385 | 401 | 400 | 355 | 390 |

Judgement: Pretreated proband sera (decomplemented and absorbed human sera) show only an unspecific complement-consumption effect and do not show an unspecific higher actual complement activity any more.

EXAMPLE 2

Test of the unspecific effect of antigen/control-antigen for CFT on the actual complement activity of a reagent mixture.

| Analytical System | 1 ml CFT-buffer contained 50 microliter complement 0,2 microliter amboceptor 1:4000 (product of Behringwerke AG, D-3550 Marburg-Marbach) |
|---|---|

To this reagent mixture as much antigen and control antigen dilutions in 100 microliter CFT-buffer was added as corresponds to the described antigen/control antigen concentration of the classic CFT. For example cytomegaly-antigen/control antigen of Behringwerke AG with a titre of 1:60. 0.25 ml antigen dilution with two units is used in the classical CFT in 1 ml reagent mixture. So, in the test the 100 microliter CFT-buffer contains 250/30=8.33 microliter undiluted dissolved antigen after reconstruction of the lyophilized product. The concentration of the control antigen is analogous.

The systems were incubated for 180 minutes at 37° C. Finally, the measurement of the actual complement activity of the systems were carried out by the CH-50%-lysis-time-analysis. To the test systems was added 100 microliter sheep-erythrocyte suspension in CFT-buffer so that the extinction value of 0.5 was obtained.

Results of different antigens and control antigens:
Cytomegaly-antigen (Behringwerke AG).

| Charge 1 | Charge 2 | Charge 3 |
|---|---|---|
| antigen 315" | 340" | 330" |
| control antigen 320" | 340" | 310" |

RUBELLA antigen (Behringwerke AG).

| Charge 1 | Charge 2 | Charge 3 |
|---|---|---|
| antigen 310" | 315" | 310" |
| control antigen 314" | 312" | 311" |
| Toxoplasmose antigen (Messrs. Biomerieux) | | |
| antigen 355" | 360" | 440" |
| control antigen 315" (blank value) | 310" | 320". |

Remark: Toxoplasmose-antigen Biomerieux is obtained from mouse ascites. For this reason there is no control antigen, just a control system. Instead of control antigen CFT-buffer is used.

Judgement: It is easy to see that the principle of the optimized visual Complement Fixation Test cannot be realized by simple mixing together of reagents, this could only be possible in exceptional cases.

The simple mixing together of reagents is only possible with highly purified, high-grade, high-quality reagents (antigen/control antigen or immune sera and control sera), which possess absolutely no or only a minimal and completely identical unspecific effect on the actual complement activity of the reagent mixture.

In these examples given this is only possible with the Rubella-CFT-antigen of Behringwerke AG. This is a highly purified antigen from tissue culture.

In all other cases suitable steps are necessary to guarantee the resynchronization of the antigen/control antigen system:

In the case of slight deviations, as for example in the cytomegaly charge no. 1, this can occur when after completion of the main incubation the starting of the indicator by the addition of sheep-erythrocyte suspension in the antigen system was displaced exactly by 5 seconds delay. By doing this it can be guaranteed that in the negative control system a synchronized haemolysis reaction ocurs. Another way to resynchronize is to determine in a series of experiments how much more complement for example the antigen system of the cytomegaly-charge-no. 3 requires, so that the CH-50%-lysis-time of −20 seconds can be balanced out. For this purpose a series of tests with increasing amounts of complement in the analytical system is carried with 50/55/60/65 etc. microliter complements in 1 ml reactant mixture. One determines a value of 57.5 microliter complement requirement in the antigen system compared to the control antigen system with 50 microliter complement in order that identical complement activities will be obtained after completion of the primary incubation.

The other possibility of resyncrhonization of the actual complement activity in the system is the determination of a dilution factor. For this purpose, in the toxoplasmose-CFT-test the control system is diluted with increasing amounts of CFT buffer before beginning the primary incubation. That is, the lyophilized reagents are diluted directly after reconstitution. To the control system (1 ml) is added 100/200/300/400/500/600 microliter CFT-buffer additionally mixed well and then the corresponding amount is removed. By this means a percentual dilution of the system with the higher actual complement activity is obtained. In the example a factor of 0.5 (=50%) was determined. This means that one had to add an additional 0.5 ml CFT-buffer to the 1 ml reactant, a further 50% dilution, so that after completion of the main incubation (180 minutes at 37° C.), despite the unspecific anticomplement activity of the antigen, both systems possess identical complement activity and so the principle of the optimized visual CFT can be realized.

The invention is not limited to the process or test package described above which may be varied in detail.

We claim:

1. A process for carrying out serological investigations according to the complement binding reaction comprising reacting an immunological reagent selected from the group consisting of an antigen and an antibody not specific for erythrocytes in a patient's serum with the immunological binding partner to said immunological reagent to form an immunocomplex, providing a quantity of complement in excess of that required for reaction with said immunocomplex, reacting said immunocomplex with said complement, determining by a kinetic method the excess complement from the reaction of said immunocomplex and said complement after incubation with erythrocytes.

2. The process of claim 1, wherein evaluating is accomplished by comparing the amount of complement in the second step and the amount of complement in a control sample with one another.

3. The process of claim 2, wherein the excess of complement in the second step and in the control is compared by
    (a) using reagents that have no effect on the actual complement activity,
    (b) using reagents having an unspecific effect on the amount of complement,
    (c) compensating a higher anticomplement activity in one reagent by adding a further amount of complement into the system, or
    (d) diluting the system with higher complement activity at the beginning of a main incubation but before beginning the binding of antibody and antigen with a suitable buffer to the identical actual complement activity.

4. The process of claim 1, wherein the remaining excess complement activity is back titrated and evaluated by the CH-50%-lysis-time-analysis with allowance for the latent phase of the complement haemolysis, plotting the resulting lysis-time against the natural logarithmic values or the concentrations of antigen or antibody, and comparing these values with a linear standard curve.

5. The process of claim 1, comprising using a proband serum wherein the unspecific amboceptor activities are eliminated with an amount of sheep-erythrocytes or with an extract of sheep-erythrocytes membranes during or after inactivation at 56° C. for 15 to 30 minutes.

6. The process of claim 2, comprising using a proband serum wherein the unspecific amboceptor activities are eliminated with an amount of sheep-erythrocytes or with an extract of sheep-erythrocytes membranes during or after inactivation at 56° C. for 15 to 30 minutes.

7. The process of claim 3, comprising using a proband serum wherein the unspecific amboceptor activities are eliminated with an amount of sheep-erythrocytes or with an extract of sheep-erythrocytes membranes during or after inactivation at 56° C. for 15 to 30 minutes.

8. The process of claim 4, comprising using a proband serum wherein unspecific amboceptor activities are eliminated with an amount of sheep-erythrocytes or with an extract of sheep-erythrocytes membranes during or after inactivation at 56° C. for 15 to 30 minutes.

9. A test reagent in ready-to-use test packages for carrying out the complement fixation test comprising
    an amboceptor specific for erythrocytes,
    complement, and
    an antigen or antibody not specific for erythrocytes, wherein all components are in solid form and said test reagent contains an excess of complement required for reaction with an immunocomplex.

* * * * *